United States Patent [19]

Brasitus et al.

[11] Patent Number: 6,040,300
[45] Date of Patent: Mar. 21, 2000

[54] METHOD OF PREVENTING COLON CANCER WITH VITAMIN $D_3$ ANALOGUES

[75] Inventors: Thomas A. Brasitus, Olympia Fields; Bruce Marc Bissonnette, Chicago; Michael D. Sitrin, Flossmoor, all of Ill.

[73] Assignee: Arch Development Corporation, Chicago, Ill.

[21] Appl. No.: 08/418,638

[22] Filed: Apr. 7, 1995

[51] Int. Cl.[7] .............................. A61F 2/02; A61K 9/20; A61K 9/48
[52] U.S. Cl. ........................ 514/167; 424/451; 424/464
[58] Field of Search ........................... 514/167; 424/423, 424/451, 464

[56] References Cited

U.S. PATENT DOCUMENTS 5,451,574  9/1995  Baggliolini et al. .................... 514/167

FOREIGN PATENT DOCUMENTS

| | | |
|---|---|---|
| 2096105 | 5/1993 | Canada . |
| 0 529 528 | 3/1993 | European Pat. Off. . |
| 0580968A2 | 2/1994 | European Pat. Off. . |

OTHER PUBLICATIONS

Shabahang et al., "A Comparison of the Antiproliferative effect of 1,25–Dihydroxyvitamin $D_3$ and Three Analogs in Colon Carcinoma Cell Lines," *Endocrinology*, Proceedings of the American Association for Cancer Research, Abstract No. 1453, 34:244, Mar. 1993.

Steele et al., "Preclinical Efficacy Evaluation of Potential Chemopreventive Agents in Animal Carcinogenesis Models: Methods and Results from the NCI Chemoprevention Drug Development Program," *Journal of Cellular Biochemistry*, Supplement 20:32–54, 1994.

Wali et al., "1α,25–Dihydroxy–16–Ene–26,27–Hexa–Fluorocholecalciferol (Ro24–5531), a Non–Calcemic Analog of 1α,25–Dihydroxyvitamin $D_3$, Inhibits Azoxymethane–Induced Colonic Tumorigenesis," *Gastroenterology*, 108(4):A550, Apr. 1995.

International Search Report dated Aug. 13, 1996.

Anzano et al., "1α,25–Dihydroxy–16–ene–23–yne–26, 27–hexafluorocholecalciferol (Ro24–5531), a New Deltanoid (Vitamin D Analogue) for Prevention of Breast Cancer in the Rat," *Canc. Res.*, 54:1653–1656, Apr. 1, 1994.

Belleli et al., "A protective role of 1,25–dihydroxyvitamin $D_3$ in chemically induced rat colon carcinogenesis," *Carcinogenesis*, 13(12):2293–2298, 1992.

Earnest et al., "Chemoprevention of Azoxymethane–induced Colonic Carcinogenesis by Supplemental Dietary Ursodeoxycholic Acid," *Canc. Res.*, 54:5071–5074, Oct. 1, 1994.

Ferrera et al., "Highly Potent Transcriptional Activation by 16–ene Derivatives of 1,25–dihydroxyvitamin $D_3$," *J. Biol. Chem.*, 269(4):2971–2981, 1994.

Fiala et al., "Inhibition of the Metabolism of the Colon Carcinogen, Azoxymethane, by Pyrazole," *Canc. Res.*, 38:4515–4521, Dec. 1978.

Garland et al., "Dietary Vitamin D and Calcium and Risk of Colorectal Cancer: A 19–Year Prospective Study in Men," *Lancet*, pp. 307–309, Feb. 9, 1985.

Garland and Garland, "Do Sunlight and Vitamin D Reduce the Likelihood of Colon Cancer," *Int. J. Epidem.*, 9(3):227–231, 1980.

Garland et al., "Can colon cancer incidence and death rates be reduced with calcium and vitamin D," *Am. J. Clin. Nutr.*, 54:193S–201S, 1991.

Halline et al., "Effects of 1,25–Dihydroxyvitamin $D_3$ on Proliferation and Differentiation of Caco–2 Cells," *Endocrinology*, 134(4):1710–1717, 1994.

(List continued on next page.)

*Primary Examiner*—Carlos A. Azpuru
*Attorney, Agent, or Firm*—Arnold White & Durkee

[57] ABSTRACT

A method for preventing the initiation of colon cancer is disclosed. Vitamin $D_3$ analogues prevented the development of adenomas and adenocarcinomas when administered to rats prior to, and subsequent to, chemically induced tumorigenesis.

13 Claims, 2 Drawing Sheets

OTHER PUBLICATIONS

Ikekawa and Ishizuka, "Molecular Structure and Biological Activity of Vitamin D Metabolites and their Analogs" *Molecular Structure and Biological Activity of Steroids,* Ch. 8, pp. 293–316, Bohl and Duax, eds., CRC Press, Boca Raton, Fl, 1992.

Kawaura et al., "Supplemental administration of 1α–hydroxyvitamin $D_3$ inhibits promoter by intrarectal instillation of lithocholic acid in N–methyl–Nenitrosourea–induced colonic tumorigenesis in rats," *Carcinogenesis,* 10(4):647–649, 1989.

Kawaura et al., "1α–Hydroxyvitamin $D_3$ suppresses colonic tumorigenesis induced by repetitive intrarectal injection of N–methyl–N–nitrosourea in rats," *Canc. Lett,* 55:149–152, 1990.

Llor et al., "K–ras Mutations in 1,2–Dimethylhydrazine–induced Colonic Tumors: Effects of Supplemental Dietary Calcium and Vitamin D Deficiency," *Canc. Res.,* 51:4305–4309, Aug. 15, 1991.

Niendorf et al., "Effect of 1,25–Dihydroxyvitamin $D_3$ on Human Cancer Cells In Vitro," *J. steroid Biochem.,* 27(4–6):825–828, 1987.

Pence and Buddingh, "Inhibition of dietary fat–promoted colon carcinogenesis in rats by supplemental calcium or vitamin $D_3$," 9(1):187–190, 1988.

Sitrin et al., "Dietary Calcium and Vitamin D Modulate 1,2–Dimethylhdrazine–induced Colonic Carginogenesis in the Rat," *Cancer Research,* 51:5608–5613, Oct. 15, 1991.

Wali et al., 1α,25–Dihydroxy–16–ene–23–yne–26, 27–hexafluorocholecalciferol, a Noncalcemic Analogue of 1α,25–Dihydroxyvitamin $D_3$, Inhibits Azoxymethane–induced Colonic Tumorigenesis[1], *Cancer Research,* 55:3050–3054, Jul. 15, 1995.

Zhou et al., "Development of a Novel 1,25–$(OH)_2$–Vitamin $D_3$ Analog with Potent Ability to Induce HL–60 Cell Differentiation Without Modulating Calcium Metabolism," *Blood,* 78(1):75–82, Jul. 1, 1992.

Willett, W., "The search for the causes of breast and colon cancer," *Nature,* 338:389–394, Mar. 30, 1989.

Zhou et al., "1,25–Dihydroxy–16–ene–23–yne–vitamin $D_3$ prolongs survival time of leukemic mice," *Proc. Natl. Acad. Sci. USA,* 87:3929–3932, May 1990.

Wilhelm et al., "6–Fluoro–Vitamin $D_3$: A New Antagonist of the Biological Actions of Vitamin $D_3$ and its Metabolites Which Interacts with the Intestinal Receptor for 1α, 25 $(OH)_2$ –Vitamin $D_3$," *Arch Biochem. Biophys,* 233(1):127–132, 1984.

METHOD OF PREVENTING COLON CANCER WITH VITAMIN $D_3$ ANALOGUES

The government owns rights in the present invention pursuant to grant number CA36745, 5P30DK26678 from the Clinical Nutrition Research Unit, and P30DK42086 from the Digestive Diseases Research Core Center, DK39573 from the U.S. Public Health Science.

BACKGROUND OF THE INVENTION

1. Field of the Invention

The present invention relates generally to the field of cancer prevention. In particular, the invention relates to a method of preventing colon cancer by vitamin $D_3$ analogues. In one example, administration of $1\alpha$, 25-Dihydroxy-16-ene-23-yne-26, 27-hexafluorocholecalciferol reduced the incidence of colon cancer in rats.

2. Description of the Related Art

Colon cancer is a leading cause of death among patients with internal malignancies in the United States and, unfortunately, at the time of initial diagnosis is incurable in approximately one-half of the patients found to harbor this malignancy (Zarling and Rhodes, Int. Med. Specialist 3:72–86, 1982). Moreover, despite advances in the fields of surgery, radiotherapy and chemotherapy, the cure rate for this disease has not improved significantly (Zarling and Rhodes, 1982). Based on these considerations, the search for strategies to prevent the development of cancers in this organ has markedly intensified during the past decade.

Although the cause of large bowel cancer is not known, most epidemiologists associate it with diet, and, in particular, the low-fiber, high-protein, high-fat content that characterizes the diet of most Americans and people in other urban, industrialized societies. Many observers believe that colon cancer is the first major cancer type for which available evidence is sufficient to recommend dietary changes in the general public (Willett, Nature 338:384, 1989; Greenwald, Cancer 70 (Suppl.): 1206, 1992). In this regard, the possibility of using dietary supplements as a strategy to prevent colon cancer has recently been recognized (Mukhtar and Athar, Clev. Clin. J. Med. 55:507–508, 1988).

During the past few years one such potential dietary supplement, vitamin $D_3$, has received increasing attention. Data has accumulated from a number of different sources in support of the possibility that vitamin $D_3$, or its metabolites, may play a preventive role in the development of colon cancer. Several epidemiological studies (Garland et al., Lancet 1:307–309, 1985; Garland et al., Int. J. Epidemiol. 9:227–231, 1980; Garland et al., Lancet II:1176–1178, 1989, Garland et al., Am J. Clin. Nutr. 54:193S–201S, 1991), for example, have suggested that vitamin $D_3$ derived from the diet or from cutaneous synthesis due to sunlight exposure may decrease the risk of colon cancer in humans. Additionally, vitamin $D_3$ dietary supplementation has been shown to inhibit the incidence of colon carcinogenesis induced by the administration of 1,2-dimethylhydrazine (DMH) in rats fed a high fat diet (Pence and Buddingh, Carcinogenesis (Lond) 9:187–190, 1988).

Both the vitamin $D_3$ metabolites, $1\alpha$-hydroxyvitamin $D_3$ ($1\alpha(OH)D_3$) (Kawaura et al., Carcinogenesis (Lond) 10:647–649, 1989, Kawaura et al., Cancer Lett. 55:149–152, 1990) and $1\alpha$,25-dihydroxyvitamin $D_3$ ($1\alpha,25 (OH)_2D_3$) (Belli et al., Carcinogenesis 13:2293–2298, 1992), have also recently been shown to protect against the development of chemically-induced colonic tumors. Furthermore, $1\alpha,25(OH)_2D_3$ has been demonstrated to inhibit the proliferation of a number of malignant cell lines in vitro (Colson et al., Endocrinology 108:1083–1086, 1981, Lointier et al., Anticancer Res. 7:817–822, 1987, Niendorf, et al., J. Steroid Biochem. 27:815–828, 1987, Tanaka et al., Arch. Biochem. Biophys. 276:415–423, 1990, Halline et al., Endocrinology 134:1710–1717, 1994), including several derived from human colon adenocarcinomas (Lointier et al., 1987, Niendorf et al., 1987, Tanaka et al., 1990, Halline et al., 1994).

While these studies have suggested that vitamin $D_3$ or one or more of its metabolites may prevent colon cancer, there is considerable concern about their potential toxicity, particularly with respect to elevation of serum $Ca^{2+}$ levels and its consequences, such as deposition of this mineral in soft tissues (Kawaura, et al., 1989, Belli, et al., 1992, Anzano, et al., Cancer Res. 54:1653–1656, 1994).

Recently, a fluorinated derivative of vitamin $D_3$, $1\alpha,25 (OH)_2$-16-ene-23-yne-26,27 $F_6$-vitamin $D_3$ (RO24-5531), was found to inhibit proliferation of HL-60 cells (Zhou et al., Blood 78:15–82, 1991), presumably because substitution of fluorine atoms on C-26 and C-27 inhibits its metabolism and prolongs its actions (Anzano et al., 1994; Zhou et al., 1991). Moreover, RO24-5531 extended breast tumor latency and lessened tumor incidence as well as tumor number, without causing elevated levels of serum $Ca^{2+}$ in these animals (Anzano et al., 1994).

In comparing breast and colon cancers, however, epidemiologic differences appear when various risk groups are studied. For example, in the United States, while Japanese immigrants have colon cancer rates similar to the Caucasian population, breast cancer rates take several generations to approach those of the resident population (Hanai et al., Nat. Can. Inst. Monograph 62:3–7, 1982, Haenszel, 1982). In a related study, the rates of breast cancer among Seventh-Day Adventists were similar to those in the general population, but rates of colon cancer were about 40% lower (Phillips et al., J. Natl. Cancer Inst. 65:1097–1107, 1980). In case-controlled and prospective cohort studies of colon and breast cancer, research indicated that clear associations were found between fat or meat intake and colon cancer, but not breast cancer, in each pair of analyses (Phillips, Cancer Res. 35:3513–3522, 1975; Willett et al., New Engl J. Med. 316:22–28, 1987). The treatment methods for colon cancer, of which more than 99% are adenocarcinomas, are generally different from those used for breast cancer treatment. In summary, with respect to natural history, epidemiological studies and treatment strategies, breast and colon cancer are substantially different.

While epidemiologic evidence implicates diet as a major etiologic factor for colorectal cancer, there exists a great need for a dietary supplement or anticarcinogen to prevent the primary initiation of tumorigenesis, without causing toxicity.

SUMMARY OF THE INVENTION

It is an object of the present invention to overcome this problem by providing a method for reducing the incidence of colon cancer by administering a nutrient supplement. The method comprises administering to a subject an effective amount of a non-calcemic analogue of vitamin $D_3$ prior to and subsequent to the initiation of tumorigenesis. The present studies demonstrate in a surprising and unexpected manner that dietary supplementation with one such analogue, $1\alpha,25$-dihydroxy-16-ene-23-yne-26,27-hexafluorocholecalciferol, can inhibit the development of colonic tumors in mammals. Moreover, this synthetic analogue of $1\alpha,25(OH)_2D_3$ appears to be well-tolerated by the animals, and does not induce hypercalcemia or alterations in the serum levels of phosphorus, $25(OH)D_3$, or $1,25(OH) 2D_3$.

MULTISTEP CARCINOGENESIS

Figure 1:
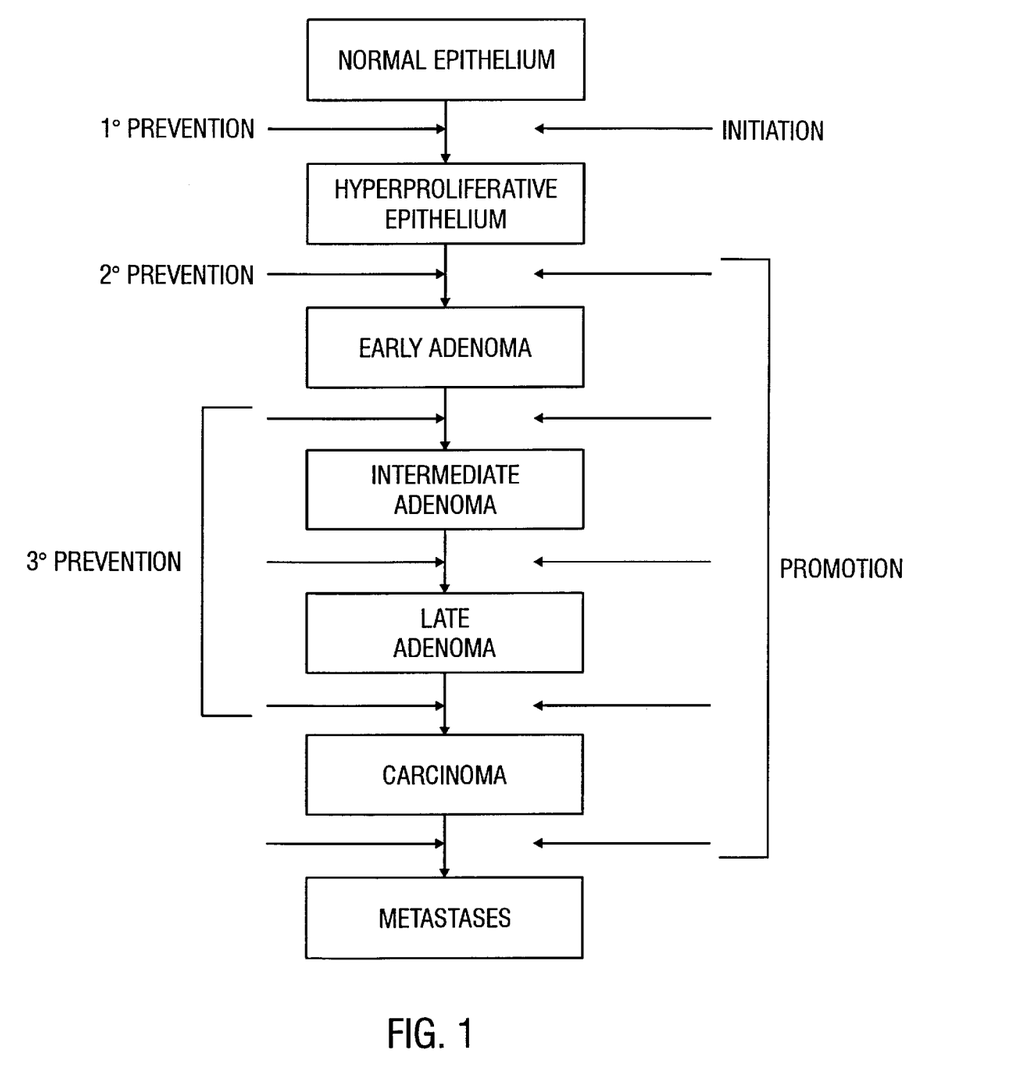
FIG. 1. Colorectal tumors arise through a series of genetic and morphological alterations.

Colon malignant transformation is a multistep event. It is thought to evolve through a series of genetic (Fearon and Vogelstein, *Cell* 61:759, 1990) and histopathologic forms. It begins with dysplastic areas of the forming in the colonic epithelium, which pass through a stage of adenomatous polyps, and ultimately progress to frank carcinoma (FIG. 1).

The first step towards colon carcinogenesis is thought to be the transformation of normal epithelial cells to hyperproliferative epithelial cells. This is represented by abnormal multiplication of epithelial cells or an increase in number of normal epithelial cells in normal arrangement, which is then followed by adenoma. Adenomas are characterized by dysplastic changes, particularly in the cell nucleus, that are frequently associated with metaplasia and carcinoma in situ. The underlying basement membrane or basal cell lamina, however, is not interrupted; that is, preneoplasia shows no evidence of microinvasion or other hallmarks of cancer behavior (Robbins et al., *Neoplasia. Pathologic Basis of Disease*, 1984). The morphological changes suggest that the preneoplastic cell is in transition from a normal to a neoplastic form.

A patient with adenoma may be classified as having early, intermediate or late adenoma depending upon the size and histological features of the adenomatous polyps, including the extent of dysplasia the adenomas possess. Patients with early to intermediate adenoma tend to have adenomatous polyps that are of a small size, sessile tubular in shape, and that are associated with mild dysplasia. While patients with intermediate to late adenoma will have more adenomatous polyps of a larger size, greater than 2 cm, tubovillous or villous in shape, with severe dysplasia. Although preneoplastic lesions may progress to neoplasia, they may also remain stable for long periods and may even regress, particularly if the initiating agent is removed.

Adenocarcinomas, are adenomas that have undergone the final step to neoplasia. This event is monoclonal, in that a single cell from either normal or preneoplastic tissue becomes neoplastic, with the expansion of that clone ultimately producing cancer (Fialkow et al., *Genetics of Human Cancer*, 1977). Microinvasion of the basement membrane characterizes the transition from preneoplasia (adenoma) to cancer (adenocarcinoma). The final step in colon malignant transformation is the release of tumor cells from the primary tumor into the blood where the dissemination of metastasis occurs, which is the major cause of death from cancer.

Each step, described herein, represents an increase in the incidence of colon malignant transformation. According to the present invention, the phrase "reducing the incidence of colon malignant transformation" is intended to refer to the cessation, or reduction in number, of any one of the steps involved in this progressive process towards cancer.

In one embodiment, reducing the incidence of colon malignant transformation may involve preventing any normal epithelial cells from transforming into hyperproliferative epithelial cells, or it may involve reducing the number of cells transforming into hyperproliferative epithelial cells. In another embodiment, reducing the incidence of colon malignant transformation may involve preventing any hyperproliferative epithelial cells from transforming into early adenomas, or it may involve reducing the number of cells transforming into early adenomas. In another embodiment, reducing the incidence of colon malignant transformation may involve preventing early adenomas from transforming into intermediate adenomas, or it may involve reducing the number of cells transforming into intermediate adenomas.

In yet another embodiment of the invention, reducing the incidence of colon malignant transformation may involve preventing any intermediate adenomas from transforming into late adenomas, or it may involve reducing the number of cells transforming into late adenomas. In a further embodiment, reducing the incidence of colon malignant transformation may involve preventing late adenomas from transforming into carcinoma or it may involve reducing the number of cells transforming into carcinoma. Finally, in another embodiment, reducing the incidence of colon malignant transformation may involve preventing any carcinoma from transforming into metastases, or it may involve reducing the number of cells transforming into metastases.

CANCER PREVENTION

For the purposes of the present invention, carcinogens may be divided into "initiators" and "promoters" (see FIG. 1; Byar, *Recent Results in Cancer Research. Cancer Clinical Trials: A Critical Appraisal*, 111:35–48, 1988). Certain agents appear to initiate cancer, while those designated as promoters are effective only after cancer has been initiated with some other agent. Some agents may act as both initiators and promoters. It is assumed that some of these initiated and promoted cells will then develop into precancerous lesions.

Adenocarcinoma designates the point at which pathologists would no longer designate lesions as preneoplastic, but would actually diagnose cancer. Prevention of the development of adenocarcinomas can, therefore, take place anywhere along the line before that point.

Cancer prevention strategies may be divided into three categories primary, secondary, and tertiary, depending on where in the carcinogenic process the preventive measure is supposed to intervene (FIG. 1) (Bertram et al. *Cancer Res.* 47:3012–3031, 1987). Primary prevention effects the initiation of carcinogenesis and represents the very first step intervention may occur. If the carcinogenic process has already begun and an attempt is made to interrupt it by decreasing cancer promotion, it may be termed secondary prevention. The subjects in primary and secondary prevention trials do not have detectable lesions, although they may be chosen to be at high risk for developing cancer. After precancerous lesions are present, tertiary prevention may begin, which goal is to alter these lesions either by making them regress or disappear, or by preventing their development into cancer.

In one embodiment of the invention, preventing the development of adenocarcinomas is a primary prevention strategy and prevents or averts the initiation of carcinogenesis. In another embodiment, preventing the development of adenocarcinomas is a secondary prevention strategy. In yet a further embodiment of the invention, preventing the development of adenocarcinomas is a tertiary prevention strategy.

VITAMIN $D_3$ ANALOGUES

Vitamin $D_3$ (cholecalciferol) is one of two vitamins D that is effective in promoting calcification of the bony structures of humans and animals. A deficiency of vitamin $D_3$ leads to inadequate absorption of calcium from the intestinal tract and retention of phosphorus in the kidney, resulting in faulty mineralization of bone structures and rickets. In advanced stages, demineralization of bones occurs, and multiple fractures may result from slight trauma. Conversely, too much vitamin $D_3$ can lead to hypercalcemia and attendant complications, such as metastatic calcification and renal calculi (Remington's Pharmaceutical Sciences, 18th ed.).

The invention involves the use of non-calcemic analogues of vitamin $D_3$ to reduce the incidence of colon malignant transformation while preventing undesirable side effects. Non-calcemic compounds may be defined as any compound that does not cause sufficient absorption of calcium to cause hypercalcemia to the subject. These compounds are used at an amount effective to reduce the incidence of colon malignant transformation.

In general hypercalcemia is assayed by measuring the amount of intestinal calcium absorption (ICA) or bone calcium mobilization (BCM) in a subject, and comparing the amount after long term injection with the amount of vitamin $D_3$ similarly administered (Zhou et al. ,1991). For the purposes of the present invention, any compound about

5-fold to about 10-fold less active than vitamin $D_3$ may be considered non-calcemic. Alternatively, the level of calcium ions in serum may be measured by atomic adsorption. Subjects with greater than about 12 mg/dl of calcium in their serum may be considered as suffering from hypercalcemia (Zhou et al., 1990). Any vitamin $D_3$ analogue, that after administration to a subject produces a serum level below approximately 2 mg/dl and with an about 5-fold to about 10-fold decrease in ICA or BCM value as compared with vitamin $D_3$, may be included in the present invention.

Vitamin $D_3$ analogues include any compound that has a similar structure to vitamin $D_3$ but differs from it, with respect to one or more components. A component is defined herein as being a single atom or ion, or a compound of one or more atoms or ions. Therefore any compound with a structural similarity to Vitamin $D_3$ may be considered in the present invention, provided that it reduces the incidence of colon malignant transformation in a subject.

To assess the ability of a vitamin $D_3$ analogue to function according to the present invention, it is a straightforward matter of administering the analogue into a subject as described in the Example. A vitamin $D_3$ analogue is administered prior to and subsequent to tumorigenesis in the subject. Subsequent adenoma and adenocarcinoma histopathology is analyzed and compared with controls. Any compounds reducing the incidence of colon malignant transformation or preventing the development of adenocarcinomas may be included in the present invention.

Alternatively, in vitro analyses may be performed on transformed of preneoplasia cell lines as described in Niendorf et al. (1987), incorporated herein by reference. Vitamin $D_3$ analogues are administered to cell cultures and inhibition of cellular proliferation is monitored. Any compounds found inhibiting cell proliferation or growth may be included in the present invention.

The invention relates to compounds of the formula

I wherein R is hydrogen, or particularly hydroxy or fluorine, and X is $H_2$ or $CH_2$. The invention also relates to intermediates of the formula

III' wherein R' is oxo, —OH or —OSi$(CH_3)_3$.

Compounds of Formula I include: 26,26,26,27,27,27-hexafluoro-25-hydroxy-16-ene-23-yne-cholecalciferol, 26,26,26,27,27,27,27-hexafluoro-1α-fluoro-16-ene-23-yne-19-nor-cholecalciferol.

In preferred embodiments, non-calcemic vitamin $D_3$ analogues may include 1,25-(OH)$_2$-16-en-23-yn-26,27-$F_6$-$D_3$, 25-OH-16-en-23-yn-26,27-$F_6$-$D_3$, 1α-F-25-OH-16-en-23-yn-26,27-$F_6$-$D_3$, 1α-F-25-OH-16-en-23-yn-26,27-$F_6$-$D_3$, 1α-(OH)-25-Oxo-25-phospha-$D_3$, 1α-(OH)-25-Oxo-26,27-dimethyl-25-phospha-26,27-dioxa-$D_3$, 24-Nor-1,25-(OH)$_2$-$D_3$. This list is not intended to be exhaustive of the various vitamin $D_3$ analogues known in the art but, rather, is exemplary of the non-calcemic compounds that may be used.

In additional embodiments, fluorinated analogues of vitamin $D_3$ are employed as described by EPA 580968 (1992), incorporated herein by reference. These embodiments include: 26,26,26,27,27,27-hexafluoro-1α,25-dihydroxy-16-ene-23-yne-cholecalciferol (RO24-5531), 26,26,26,27,27,27-hexafluoro-25-dihydroxy-16-ene-23-yne-cholecalciferol, 26,26,26,27,27,27-hexafluoro-1α-fluoro-25-hydroxy-16-ene-23-yne-cholecalciferol, and 26,26,26,27,27,27-hexafluoro-1α,25-dihydroxy-16-ene-23-yne-19-nor-cholecalciferol.

It is recognized that the compounds disclosed in the instant application are intended to be representative of non-calcemic vitamin $D_3$ analogues that may be used. Alternatively, it is recognized that modifications to the ring structure of vitamin $D_3$ that produce non-calcemic vitamin $D_3$ analogues are also considered within the scope of the instant invention.

ADMINISTRATION

In order for the incidence of colon malignant transformation to be reduced, the vitamin $D_3$ analogue needs to be administered to the subject in an effective amount. In exemplary embodiments, the vitamin $D_3$ analogue is administered orally or by subcutaneous injection.

An effective amount may be considered to be any concentration of vitamin $D_3$ analogue that produces a reduction in the incidence of colon malignant transformation, as described above. This effective amount may be taken frequently over a long term basis or infrequently on a short term basis. An effective amount may encompass any administering regime, as long as it functions according to the present invention.

In preferred embodiments, compositions for oral administration comprise of an effective amount of the vitamin $D_3$ analogue, such as RO24-5531, in crystalline or powdered form. Compositions may be taken as a tablet, or powder, or capsule, or even as an ingredient in prepared food. The vitamin $D_3$ analogue may also be orally administered in liquid form, dissolved or dispersed in a pharmaceutically acceptable carrier or aqueous medium.

In addition to the compounds formulated for oral administration, other pharmaceutically acceptable forms may be prepared for subcutaneous injection. Typically, compositions can be prepared as injectables, either as liquid solutions or suspensions. Solid forms suitable for using to prepare solutions or suspensions upon the addition of a liquid prior to injection can also be prepared, and the preparations can also be emulsified.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Compositions of the vitamin $D_3$ analogue, as free base or pharmacologically acceptable salts, can be prepared in water suitably mixed with a surfactant, such as hydroxypropylcellulose. Dispersions can also be prepared in gelatin, glycerol, liquid polyethylene glycols, and mixtures thereof and in oils. Under ordinary conditions of storage and use, these preparations contain a preservative to prevent the growth of microorganisms.

A vitamin $D_3$ analogue may be formulated into a composition in a neutral or salt form. Pharmaceutically acceptable salts include the acid addition salts (formed with the free amino groups of the protein), and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The carrier can also be a solvent or dispersion medium containing, for example, water, ethanol, gelatin, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

Upon formulation, compositions will be administered in a manner compatible with the dosage formulation and in such amount as is therapeutically effective. The formulations are easily administered in a variety of dosage forms, as described above, such as tablets, time release capsule, powder, food or drink ingredient, or subcutaneous injection.

DETAILED DESCRIPTION OF THE PREFERRED EMBODIMENTS

Based on the present data, the chemopreventitive effects of dietary RO24-5531 supplementation on colon cancer appear to involve the initiation stage(s) of the multistage colonic malignant transformation process(es). In this regard, AOM, like DMH, is a colonic procarcinogen that requires metabolic activation in the host (Fiola et al., Cancer Res. 38:4515–4521, 1978; Brasitus et al., J. Clins. Invest. 77:831–840, 1986). The initiating event(s) for tumor production by these compounds has been shown to be related to aberrant DNA methylated adducts, such as $O^6$-methylguanine, generated by methyldiazonium ions (Fiola et al., 1978; Jacoby et al., J. Clin. Invest. 87:624–630, 1991). It is, therefore, possible that the inhibitory actions of RO24-5531 on tumor initiation in this model might, at least in part, involve inhibition of AOM metabolism, as has been reported for other chemopreventitive agents, such as pyrazole (Fiola et al., 1978). Alternatively, the inventor has recently shown that DMH, via induction of $O^6$-methylguanine adduct formation, induces G to A mutations in the K-ras proto-oncogene in a high percentage of DMH-induced tumors as well as in the premalignant colonic mucosa of rats treated with this carcinogen (Jacoby et al., 1991; Llor et al., Cancer Res. 51:4305–4309, 1991). These latter findings suggest that K-ras mutations may be an early, perhaps initiating, event in the colonic carcinogenesis process(es), at least in this test model. Such mutations have, in fact, more recently also been reported in AOM-induced colonic aberrant crypts, which may be the earliest recognizable precursor lesions of colon cancer in this model (Stopera et al., Carcinogenesis 13:2081–2085, 1992). Moreover, the inventor has demonstrated that the vitamin D status of rats can modulate the frequency of K-ras mutations in DMH-induced tumors (Llor et al., 1991). It is, therefore, possible that RO24-5531 might, at least in part, inhibit the initiation stage of AOM-induced colonic carcinogenesis via effects on K-ras mutations.

Colonic carcinogens, such as AOM and DMH, are also known to cause early cell degeneration and death, followed by stimulation of crypt cell division, leading to colonic cellular hyperproliferation (Belli et al., 1992; Chang, W. W. L., 1984; Sunter, J. P., Scand. J. Gastroenterol. (Supp.) 104:45–55, 1984). This latter event is considered to be a early critical step in the colonic malignant transformation process(es) (Craven et al., *J. Clin. Invest.* 79:532–541, 1987), presumably because this enhanced proliferation reinforces the aforementioned mutagenic actions of these carcinogens by promoting aberrant DNA adducts to become permanent mutations (Lipkin, M., *Cancer* 34 (Supp.) :787–888, 1974).

The colonic epithelial cell hyperproliferation produced by these carcinogens has been attributed to alterations in polyamine metabolism, i.e., increases in ornithine decarboxylase (ODC) activity during the preneoplastic period (Belli et al., 1992; Luk et al., *Cancer Res.* 46:4449–4452, 1986), and/or to increased colonic mucosal c-myc protein and mRNA expression (Yander et al., 1985; Tulchin et al., 1988). Interestingly, in this regard, while the effects of RO24-5531 on carcinogen-induced increases in ODC have not been examined to date, $1\alpha,25(OH)_2D_3$ and other metabolites of vitamin $D_3$ have been shown to inhibit the increase in colonic mucosal ODC induced by various chemical carcinogens in the preneoplastic period (Kawaura et al., 1990; Belliet al., 1992; Hashiba et al., *Cancer Res.* 47:5031–5035, 1987). Moreover, RO24-5531 (Zhou et al., 1991), like $1\alpha,25(OH)_2D_3$ (Reitsma et al., 1983), has been shown to decrease c-myc mRNA expression in HL-60 cells, concomitant with inhibition of proliferation and induction of differentiation in these cells. Taken together, these studies would suggest that the anticarcinogenic actions of supplemental dietary RO24-5531 observed in the initiation arm of the present studies may, at least in part, be ascribed to its effects on cellular proliferation and/or differentiation.

Other investigators have previously suggested that the colonic chemopreventitive effects of vitamin $D_3$ metabolites might also involve: 1) elevations of serum $Ca^{2+}$ (Sitrin et al., *Cancer Res.* 51:5608–5613, 1991; Hashiba et al., 1987); or 2) alterations in the immune function(s) of the host (Kawaura et al., 1989). Since, in the present studies, administration of supplemental dietary RO24-5531 did not result in hypercalcemia, the inventors believe the first possibility can be dismissed. The second possibility is of particular interest in that there is now increasing evidence that $1,25(OH)_2D_3$ is involved in the regulation of the immune system (Thomasset, M., *Path. Biol.* 42:163–172, 1994).

This secosteroid, for example, can promote suppressor T cell activity as well as effect the expression of class II antigens by monocytes and lymphocytes (Thomasset, M., 1994). It is, therefore, possible that $1,25(OH)_2D_3$ or related compounds, such as RO24-5531, might influence the phenomenon of "tumor surveillance" by the host, thereby accounting for their chemopreventive actions. In this regard, the inventor has shown that the administration of AOM induced alterations in the expression of MHC class I and II antigens in premalignant rat colonocytes (Rigas et al., *Immunology* 83:319–323, 1994). Moreover, in this model, the inventors have also shown that the chemopreventive effects of two other agents, ursodeoxycholic acid and piroxicam, on colonic tumor formation were paralleled by alterations in the expression of these antigens (Rigas et al., 1994).

Prior studies by Anzano et al. (Anzano et al., 1994) demonstrated that dietary supplementation with RO24-5531 protected against the development of NMU-induced breast cancers when fed to animals after administration of this carcinogen. In the present studies, however, while there was a trend for dietary RO24-5531 supplementation during the post-initiation arm to decrease AOM-induced colonic tumors, this did not reach statistical significance. Moreover, it is interesting to note that in the present studies, this dietary regimen, like its initiation arm counterpart, was associated with a complete absence of AOM-induced adenocarcinomas.

Regardless of the mechanism(s) involved, however, the present studies have demonstrated for the first time that dietary supplementation with $1\alpha,25$-dihydroxy-16-ene-23-yne-26,27-hexafluorocholecalciferol can inhibit the development of colonic tumors in the AOM model. Moreover, this synthetic analogue of $1\alpha,25(OH)_2D_3$ appeared to be well-tolerated by the animals and did not induce hypercalcemia or alterations in the serum levels of phosphorus, $25(OH)D_3$ or $1,25(OH)2D_3$.

The compounds of Formula I are generally prepared by the following schemes.

SCHEME I

In above Formula Scheme I, the compound of formula II, a known compound, is converted to the compound of formula III by reaction with a base, such as, n-butyllithium, and hexafluoracetone. The reaction is conducted in an ether solvent such as tetrahydrofuran ab about −50° C. to about −100° C. The compound of formula III is recovered by quenching the reaction, followed by a conventional work-up and a purification, e.g. by chromatography.

The compound of formula V is reacted with n-butyllithium and the compound of formula VI, preferably in a mixture of hexane and tetrahydrofuran at a temperature of about −75° C. to give a compound of formula I after removal of silyl protecting groups, conveniently with tetrabutylammonium fluoride in tetrahydrofuran solvent.

SCHEME II

In reaction Scheme II, the compound of formula III is deprotected to give the compound of formula IV by reaction with tetrabutylammonium fluoride in an ether solvent such as, tetrahydrofuran. The compound of formula IV is reacted with pyridinium chlorochromate in a chlorinated hydrocarbon solvent such as methylene chloride at room temperature to give the compound of formula V. The compound of formula I is prepared by a process which comprises reacting the compound of formula

V with n-butyllithium and a compound of formula wherein R" is H, OH, F or $OSi(CH_3)_2$t.Bu and t.Bu is tert-butyl and Ph is phenyl, in a solvent at low temperature to give the compound formula I after removal of the silyl protecting group(s).

The compounds of formula VI are known (when X is $H_2$ and R" is $OSi(CH_3)_2$ tert-butyl) or can be prepared according to known methods.

The following example is included to demonstrate preferred embodiments of the invention. It should be appreciated by those of skill in the art that the techniques disclosed in the example that follow represent techniques discovered by the inventor to function well in the practice of the invention, and thus can be considered to constitute preferred modes for its practice. Those of skill in the art should, however, in light of the present disclosure, appreciate that many changes can be made in the specific embodiments that are disclosed and still obtain a like or similar result without departing from the spirit and scope of the invention. Unless defined otherwise, all technical and scientific terms used herein have the same meaning as commonly understood by one of ordinary skill in the art to which this invention belongs.

EXAMPLE I

A. MATERIALS & METHODS

1. Chemicals and Feed

RO24-5531 was provided by Hoffmann LaRoche Inc. (Nutley, NJ; EP 580968). All diets were obtained from ICN Biochemicals (Cleveland, Ohio). Prior to pelleting, RO24-5531 or vehicle (0.1% ethanol) were mixed with the standard vitamin D-sufficient diet by ICN Biochemicals. This diet has been described in detail (Sitrin et al., 1991) and contained a normal content of calcium and phosphorus, 0.87% and 0.60%, respectively, with 2.2 IU of vitamin $D_3$/g of feed.

2. Protocol of Study

Figure 2:
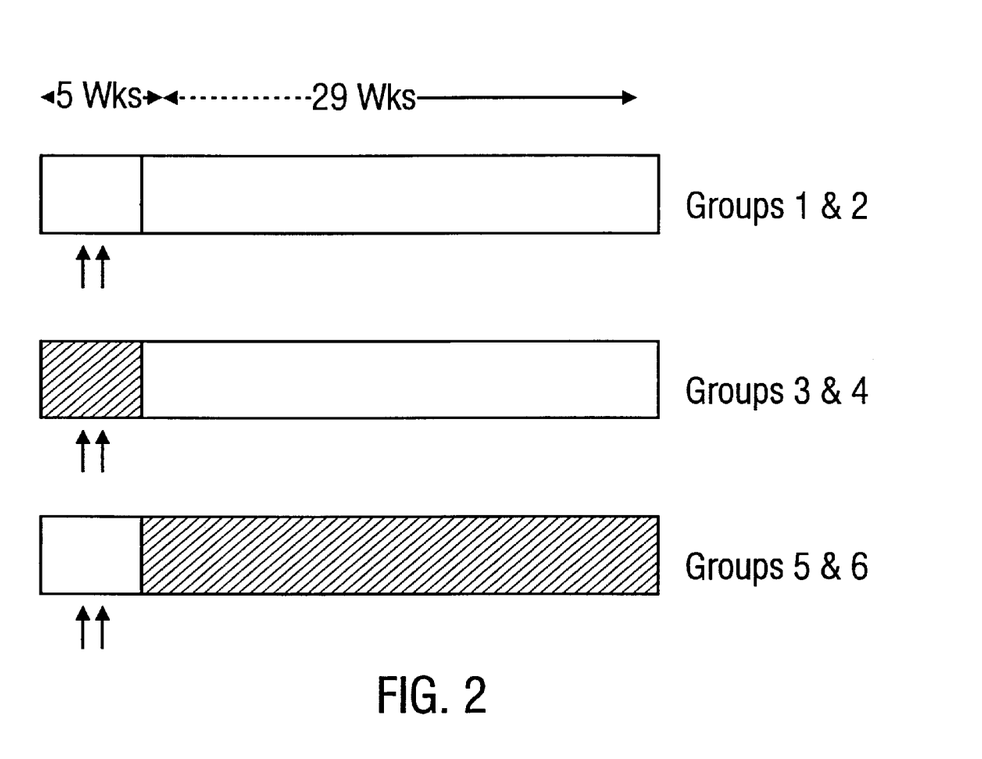
FIG. 2. Study Protocol: Rats (12 each, in groups 1,3 and 5; 20 each, in groups 2,4 and 6) were fed either standard diet without RO24-5531 (open bars), or RO24-5531 supplemented diets (shaded bars) for the initial five weeks of the study. During this period rats were given two weekly subcutaneous injections of either AOM (15 mg/kg body wt/wk) (groups 2,4 or 6), or AOM-vehicle (saline) (groups 1,3, or 5) at the end of weeks 2 and 3 (arrows). At the end of five weeks, rats in groups 1–2 were continued on the standard diet without RO24-5531; groups 3–4 were switched to standard diet without RO24-5531; and groups 5–6 were switched to the RO24-5531 supplemented diet for another 29 weeks.

Male albino Fisher-344 rats, initially weighing ~90–100 g, were used in these studies. On arrival, the animals were quarantined for 1 wk and then randomly divided into the following six test groups: groups 1 and 2, standard vitamin D-sufficient diet; groups 3 and 4, standard diet supplemented with RO24-5531 (2.50 nmol/kg of feed); and groups 5 and 6, standard vitamin D-sufficient diet. As shown in FIG. 2, all rats (12 each in groups 1,3 and 5, and 20 each in groups 2,4 and 6) were fed their assigned diets for 2 weeks. Next, the rats in groups 2,4 and 6 were given subcutaneous injections of azoxymethane (AOM, Sigma Chemical Co., St. Louis, Mo.), 15 mg/kg body wt once a wk for 2 wks, while the rats in groups 1,3 and 5 received AOM-vehicle (saline).

Groups 1 and 2 were then maintained on the standard diet for an additional 30 wks. Groups 3 and 4 were maintained on the RO24-5531 supplemented diets for the initial five wks and then switched to the standard diet without RO24-5531 for an additional 29 wks (initiation arm), whereas groups 5 and 6 were maintained on the standard diet without supplemental RO24-5531 for the initial five wks and then switched to the RO24-5531 supplemented diet for an additional 29 wks (post-initiation arm).

All rats were sacrificed in the non-fasting state after 34 wks on these protocols between 9 a.m. and 11 a.m. and sera obtained for measurement of calcium, phosphate, $25(OH)D_3$ and $1\alpha,25(OH)_2D_3$ levels. The rats' colons were removed, opened, washed with normal saline and examined macroscopically for the presence of tumors. Resected tumors were weighed, and were fixed in 10% buffered formalin for microscopic examination. After formalin fixation, tissue specimens were paraffin-embedded, sectioned, and stained with hematoxylin and eosin as described previously (Sitrin et al., 1991), for light microscopic examination. All specimens were evaluated by a pathologist who was unaware of the dietary or AOM treatment history. Macroscopic and microscopic lesions were classified as either benign (adenoma) or malignant (adenocarcinoma).

3. Measurement of Serum Calcium, Phosphorus, 25(OH) $D_3$ and $1,25(OH)_2D_3$ Levels Serum calcium and phosphorus were measured by standard colorimetric methods (Kessler and Wolfman, *Clin. Chem.* 10:686–703, 1964). Serum $25(OH)D_3$ levels were measured by radioimmunoassay, using a kit and procedure supplied by Incstar (Stillwater, Minn.). Serum $1\alpha,25(OH)_2D_3$ levels were assayed by a non-equilibrium competitive protein-binding assay based on a calf thymus receptor, using a kit and procedure supplied by Incstar, as previously described (Sitrin et al., 1991).

4. Statistical Methods

Results are expressed as means ±SE of n determinations. Data were analyzed by Fisher's exact test (two-tailed) or analysis of variance (ANOVA) as appropriate (Snedecor and Cochran, *Statistical Methods*, 1980). Values of p <0.05 were considered statistically significant.

B. RESULTS

1. General Observations

The initial weights of the animals studied in the six groups ranged from 92±15 g to 102±12 g. At sacrifice, the final weights of the animals ranged from 465±16 g to 511±30 g (Table 1). Thus, neither the RO24-5531 supplemental dietary regimens, nor the administration of carcinogen influenced the growth of the animals in any group in the present studies. Moreover, neither supplementation of the diet with RO24-5531 prior to and during AOM administration (group 4, initiation arm), nor after treatment with this carcinogen (group 6, post-initiation arm) significantly altered the serum levels of calcium, phosphorus or 25(OH)D$_3$ (Table 1). Serum 1α,25(OH)$_2$D$_3$ levels were measured in all the test groups of animals using a calf thymus receptor assay and no differences were observed.

2. Colonic Tumors

None of the control animals given injections of the AOM-vehicle and fed either the standard or RO24-5531 supplemented diets developed tumors (Table 2). In agreement with prior observations (Earnest et al., *Cancer Res.* 54:5071–5074, 1994), however, 50% of rats administered AOM and fed the standard diet (group 2) developed colonic tumors. In this group, 60% of the tumors were adenomas, whereas 40% were moderately well-differentiated adenocarcinomas (Table 2).

When compared to the group treated with carcinogen and fed the standard diet (group 2), rats fed RO24-5531 prior to and during administration of AOM (group 4, initiation arm) showed significant decreases in the incidence of colonic tumors, (Table 2). Moreover, all of the colonic tumors in group 4 (initiation arm) were found to be benign, i.e., adenomas. There was also a trend for a decrease in the number of tumors in rats fed RO24-5531 after AOM administration (group 6, post-initiation arm) compared to the AOM alone animals (group 2). Although, this did not reach statistical significance (p >0.05), in this arm of the study all of the colonic tumors were found to be adenomas. The mean weights of the tumors as well as the number of tumors/tumor-bearing rat, however, were not found to be different in the three groups (groups 2,4 and 6) administered AOM (Table 2).

TABLE 1

EFFECTS OF RO24-5531 DIETARY SUPPLEMENTATION AND AZOXYMETHANE TREATMENT ON BODY WEIGHTS OF ANIMALS AND SERUM CALCIUM, PHOSPHORUS AND 25(OH)D3[a]

| Groups | Diets[b] | Carcinogen Treatment | (N) | Initial (g) | Final Wt. (g) | Serum Levels Cas+ (mg/dl) | P (mg/dl) (n) | 25(OH)D3 (ng/ml) |
|---|---|---|---|---|---|---|---|---|
| 1 | SD[c] | − | (12) | 94 ± 12 | 466 ± 31 | 11.0 ± 0.4 (7) | 9.4 ± 0.9 (5) | 38 ± 2 (5) |
| 2 | SD | + | (20) | 96 ± 14 | 476 ± 19 | 10.7 ± 0.3 (6) | 10.1 ± 1.1 (4) | 40 ± 5 (6) |
| 3 | RO24-5531/SD | − | (12) | 101 ± 11 | 470 ± 20 | 11.3 ± 0.1 (10) | 10.2 ± 0.7 (10) | 31 ± 2 (6) |
| 4 | RO24-5531/SD | + | (20) | 92 ± 15 | 465 ± 16 | 10.1 ± 0.4 (6) | 9.9 ± 0.8 (5) | 29 ± 2 (6) |
| 5 | SD/RO24-5531 | − | (12) | 102 ± 12 | 511 ± 30 | 10.3 ± 0.4 (14) | 9.2 ± 0.3 (6) | 33 ± 4 (6) |
| 6 | SD/RO24-5531 | + | (20) | 100 ± 14 | 499 ± 28 | 10.1 ± 0.5 (8) | 9.0 ± 0.8 (11) | 36 ± 5 (6) |

(N) = number of animals studies in each group
(n) = number of separate biochemical analyses performed in each group
[a] = values represent means ± S.E.M.
[b] = see Materials & Methods Section for details of dietary treatments
[c] = standard diet
N.B. No significant differences (by ANOVA) were observed among the experimental groups for all of these measurements.

TABLE 2

EFFECTS OF RO24-5531 DIETARY SUPPLEMENTATION AND AZOXYMETHANE TREATMENT ON INCIDENCE OF TUMORS, TUMORS/TUMOR BEARING RAT, TUMOR WT AND TUMOR TYPE

| Groups | Diets[a] | AOM Treatment | No. of Animals | No. of Tumors Benign No. | Malignant No. | Total No. | No. of Tumor-Bearing Rats (% of Incidence) | Tumors/Tumor Bearing Rat | Tumor Wt. (mg) |
|---|---|---|---|---|---|---|---|---|---|
| 1 | SD[b] | − | 12 | 0 | 0 | 0 | 0 | 0 | — |
| 2 | SD | + | 20 | 6 | 4 | 10 | 10(50%) | 1.0 | 100 ± 22 |
| 3 | RO24-5531/SD | − | 12 | 0 | 0 | 0 | 0 | 0 | − |
| 4 | RO24-5531/SD | + | 20 | 3 | 0 | 3[c] | 3(15%)[c] | 1.0 | 102 ± 28 |
| 5 | SD/RO24-5531 | − | 12 | 0 | 0 | 0 | 0 | 0 | − |
| 6 | SD/RO24-5531 | + | 20 | 6 | 0 | 6 | 6(30%) | 1.0 | 109 ± 32 |

[a] = see Materials & Methods Section for details of dietary treatment.
[b] = standard diet
[c] = p < 0.05 compared to values in group 2 (Fisher's exact test)

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of reducing the incidence of colon malignant transformation in a subject comprising administering to the subject an effective amount of a non-calcemic analogue of Vitamin $D_3$.

2. The method of claim 1, wherein said non-calcemic analogue of Vitamin $D_3$ is selected from the group consisting of 26,26,26,27,27,27-hexafluoro-1α,25-dihydroxy-16-ene-23-yne-cholecalciferol (RO24-5531), 26,26,26,27,27,27-hexafluoro-25-dihydroxy-16-ene-23-yne-cholecalciferol, 26,26,26,27,27,27-hexafluoro-1α-fluoro-25-hydroxy-16-ene-23-yne-cholecalciferol, and 26,26,26,27,27,27-hexafluoro-1α,25-dihydroxy-16-ene-23-yne-19-nor-cholecalciferol.

3. The method of claim 2, wherein said non-calcemic analogue of Vitamin $D_3$ is 26,26,26,27,27,27-hexafluoro-1α,25-dihydroxy-16-ene-23-yne-cholecalciferol (RO24-5531).

4. The method of claim 2, wherein said non-calcemic analogue of Vitamin $D_3$ is 26,26,26,27,27,27-hexafluoro-25-dihydroxy-16-ene-23-yne-cholecalciferol.

5. The method of claim 2, wherein said non-calcemic analogue of Vitamin $D_3$ is 26,26,26,27,27,27-hexafluoro-1α-fluoro-25-hydroxy-16-ene-23-yne-cholecalciferol.

6. The method of claim 2, wherein said non-calcemic analogue of Vitamin $D_3$ is 26,26,26,27,27,27-hexafluoro-1α,25-dihydroxy-16-ene-23-yne-19-nor-cholecalciferol.

7. The method of claim 1, wherein said administering is oral administration.

8. The method of claim 1, wherein said administering is subcutaneous injection.

9. A method of preventing the development of adenocarcinomas in colon tissues by administering a composition, comprising a non-calcemic analogue of Vitamin $D_3$.

10. The method of claim 9, wherein said administering is prior to the development of adenocarcinomas.

11. The method of claim 9, wherein said administering is subsequent to the development of adenocarcinomas.

12. The method of claim 9, wherein said development of adenocarcinomas in colon tissues is chemically induced.

13. The method of claim 12, wherein said development of adenocarcinomas in colon tissues is chemically induced by AOM or DMH.

* * * * *